US00PP21746P2

(12) United States Plant Patent
Pieters

(10) Patent No.: US PP21,746 P2
(45) Date of Patent: Mar. 1, 2011

(54) ***CHRYSANTHEMUM* PLANT NAMED 'PPP GIRO 09'**

(50) Latin Name: *Chrysanthemum morifolium*
Varietal Denomination: PPP GIRO 09

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 24 days.

(21) Appl. No.: 12/462,274

(22) Filed: Aug. 1, 2009

(51) Int. Cl.
*A01H 5/00* (2006.01)

(52) U.S. Cl. ..... Plt./287

(58) Field of Classification Search ..... Plt./287
See application file for complete search history.

(56) References Cited

U.S. PATENT DOCUMENTS

| | | | | |
|---|---|---|---|---|
| PP11,300 P * | 3/2000 | Boeder | ..... | Plt./287 |
| PP13,891 P3 * | 6/2003 | Pieters | ..... | Plt./291 |
| PP14,501 P3 * | 2/2004 | Pieters | ..... | Plt./292 |

* cited by examiner

*Primary Examiner*—Wendy C. Haas
(74) *Attorney, Agent, or Firm*—Mark Bourgeois

(57) ABSTRACT

A new and distinct *Chrysanthemum* plant cultivar is disclosed, characterized by large decorative type inflorescences, consistent flowering response to short days, blooming consistently after 49 days of short day length, purple pink ray florets, free branching habit, and a consistent natural season flowering habit during the second week in August.

1 Drawing Sheet

Latin name of the genus and species: *Chrysanthemum morifolium.*

Variety denomination: 'PPP GIRO 09'.

BACKGROUND OF THE INVENTION

The new cultivar 'PPP GIRO 09' is a product of a cross between the male parent 'Cleagar VZP1' (U.S. Plant Pat. No. 11,300) and the female parent 'GEDI ONE JAM' (U.S. Plant Pat. No. 13,891). The new cultivar was discovered and selected by Dirk Pieters in October of 2001 in a greenhouse in Oostnieuwkerke, Belgium.

Asexual reproduction of the new cultivar 'PPP GIRO 09' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP GIRO 09' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP GIRO 09.' These characteristics in combination distinguish 'PPP GIRO 09' as a new and distinct *Chrysanthemum* cultivar:

1. Large, purple pink, decorative-type inflorescences;
2. Consistent natural season flowering habit during the second week of August;
3. Free branching habit; and
4. Consistent flowering response to short days, blooming consistently after 49 days of short day length.

Plants of the new cultivar 'PPP GIRO 09' are similar to plants of the male parent variety, 'Cleagar VZP1' in most horticultural characteristics; however plants of the new cultivar 'PPP GIRO 09' are shorter. Also, the new cultivar 'PPP GIRO 09' has a slightly larger inflorescence diameter and longer inflorescence longevity. Additionally, the ray florets of 'PPP GIRO 09' are a lighter purple than the male parent. Finally, 'PPP GIRO 09' is shorter than the male parent.

Plants of the new cultivar 'PPP GIRO 09' are similar to plants of the female parent variety, 'GEDI ONE JAM' in most horticultural characteristics, however plants of the new cultivar 'PPP GIRO 09' are shorter and have a smaller plant spread. Also, the new cultivar 'PPP GIRO 09' has a smaller inflorescence diameter. Additionally, the ray florets of 'PPP GIRO 09'are a darker purple than the female parent. Finally, 'PPP GIRO 09' naturally blooms three weeks earlier than the female parent 'GEDI ONE JAM.'

In comparison to the commercially available variety 'GEDI TWO PAD' (U.S. Plant Pat. No. 14,501), 'PPP GIRO 09' is shorter and has a smaller plant spread. Additionally, the new variety 'PPP GIRO 09' has a larger inflorescence diameter and lighter purple ray florets. Finally, 'PPP GIRO 09' blooms two weeks earlier than 'GEDI TWO PAD'.

BRIEF DESCRIPTION OF THE PHOTOGRAPH

The accompanying photograph in the drawing illustrates in full color a typical plant of 'PPP GIRO 09' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP GIRO 09' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP GIRO 09.'

Commercial classification: Garden-type *Chrysanthemum.*

PROPAGATION

Time to rooting: 7 to 14 days at approximately 21° C.

Root description: Fine, fibrous.

PLANT

Growth habit: Mounding herbaceous perennial.

Height: Approximately 17 cm.

Plant spread: Approximately 32 cm.

Growth rate: Moderate.

Branching characteristics: Free Branching.

Length of lateral branches: Approximately 13 cm.

Number of leaves per lateral branch: Approximately 24.

Age of plant described: Approximately 140 days.

FOLIAGE

Leaf:

*Arrangement.*—Alternate single.

*Average length.*—Approximately 5.3 cm.

*Average width.*—Approximately 4.7 cm.

*Shape of blade.*—Ovate.

*Apex.*—Acuminate.

*Base.*—Attenuate.

*Attachment.*—Stalked.

*Margin.*—Serrate.

*Texture of top surface.*—Lightly pubescent.

*Texture of bottom surface.*—Lightly pubescent.

*Leaf internode length.*—Approximately 0.7 cm.

*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.

*Venation.*—Type: Palmately net. Venation color upper side: Near Green 138B. Venation color underside: Near Green 138B.

Petiole:

*Average length.*—Approximately 1.4 cm.

*Color.*—Near Green 138B.

*Diameter.*—Approximately 0.3 cm.

BLOOM

Inflorescence:

*Flowering habit.*—Induced by darkness period greater than 13.5 hours, approximately 49 days of appropriate day length required to induce and develop blooms.

*Inflorescence form.*—Decorative.

*Natural flowering season.*—Approximately the second week of August.

*Number of inflorescences per lateral branch.*—Approximately 10.

*Inflorescence diameter.*—Approximately 4.8 cm.

*Inflorescence depth.*—Approximately 1.2 cm.

*Inflorescence longevity on plant.*—Approximately 28 to 34 days.

*Persistence.*—Persistent.

Ray florets:

*Appearance.*—Matte.

*Texture.*—Smooth.

*Average number of ray florets per inflorescence.*—160.

*Shape.*—Oblanceolate.

*Aspect.*—Flat.

*Margin.*—Entire.

*Apex.*—Obtuse.

*Length.*—Approximately 2.3 cm.

*Width.*—Approximately 1.3 cm.

*Color.*—Upper surface at first opening: Near Red-Purple 67A. Upper surface at maturity: Near Red-Purple 67C. Upper surface at fading: Near Red-Purple 65A. Under surface at first opening: Near Red-Purple 67B. Under surface at maturity: Near Red-Purple 67C. Under surface at fading: Near Red-Purple 65B.

Disc florets:

*Appearance.*—Shiny.

*Texture.*—Smooth.

*Average number of florets per disc.*—Approximately 16.

*Shape.*—Cylindric.

*Apex.*—Obtuse.

*Average length.*—Approximately 0.3 cm.

*Average width.*—Approximately 0.1 cm.

*Color.*—At first opening: Near Yellow-Orange 21A. At maturity: Near Yellow-Orange 21B. At fading: Near Yellow-Orange 21B.

Peduncle:

*Length.*—At terminal end (shortest): Approximately 6.5 cm. At lateral end (longest): Approximately 8.2 cm.

*Angle to stem.*—Acute.

*Strength.*—Moderate.

*Color.*—Near Green 137C.

*Habit.*—Upright.

*Diameter.*—Approximately 0.1 cm.

*Surface texture.*—Lightly pubescent.

Inflorescence bud:

*Length.*—Approximately 0.5 cm.

*Diameter.*—Approximately 0.7 cm.

*Form.*—Globular.

*Color.*—Near Green 138C.

Involucral bracts (phyllaries):

*Appearance.*—Matte.

*Texture.*—Lightly pubescent.

*Number.*—Approximately 24.

*Shape.*—Lanceolate.

*Margin.*—Entire.

*Apex.*—Obtuse.

*Length.*—Approximately 0.4 cm.

*Width.*—Approximately 0.3 cm.

*Color.*—Upper side: Near Green 138C. Under side: Near Green 138C.

REPRODUCTIVE ORGANS

Ray florets:

*Number of pistils per floret.*—1.

*Stigma shape.*—2 branched.

*Stigma color.*—Near Yellow 9A.

*Style color.*—Near Yellow-Green 154C.

*Style length.*—Approximately 0.4 cm.

*Stamens.*—Absent.

Disc florets:

*Number of pistils per floret.*—1.
*Stigma shape.*—Cylindric.
*Stigma color.*—Near Yellow 9A.
*Style length.*—Approximately 0.1 cm.
*Style color.*—Near Yellow-Green 154D.
*Number of stamens per floret.*—Approximately 5.
*Anther shape.*—Tubular.
*Anther color.*—Near Yellow 9A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP GIRO 09' as herein illustrated and described.

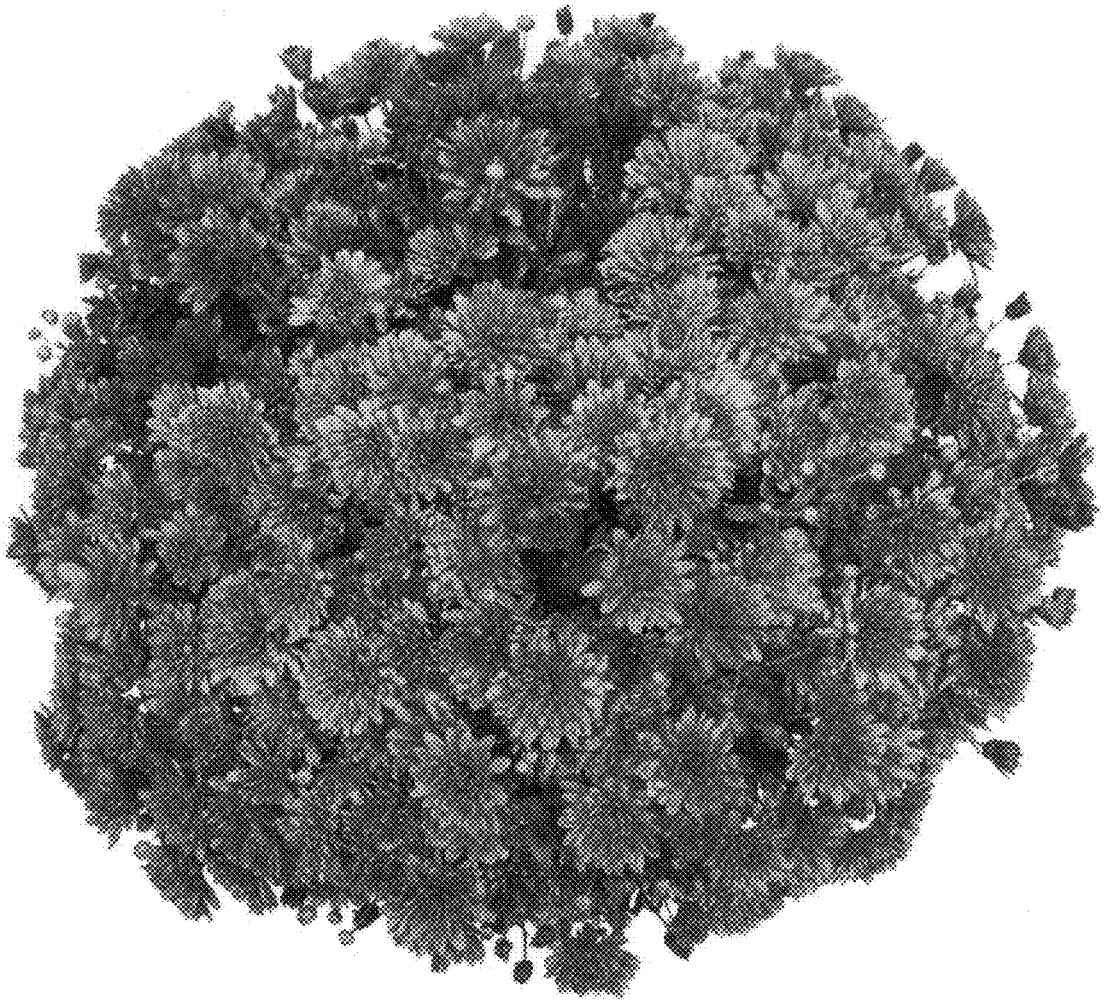

* * * * *